US00PP08077P

United States Patent [19]

Zampini

[11] Patent Number: Plant 8,077

[45] Date of Patent: Dec. 29, 1992

[54] GREEN ASH TREE NAMED CIMMZAM

[75] Inventor: James W. Zampini, 5052 S. Ridge Rd., Perry, Ohio 44081-0122

[73] Assignee: James W. Zampini, Perry, Ohio

[21] Appl. No.: 639,839

[22] Filed: Jan. 10, 1991

[51] Int. Cl.[5] ..... A01H 5/00

[52] U.S. Cl. ..... Plt./53.1

[58] Field of Search ..... Plt./51, 53.1

[56] References Cited

U.S. PATENT DOCUMENTS

P.P. 7,036 9/1989 Wandell ..... Plt. 51

*Primary Examiner*—James R. Feyrer

*Attorney, Agent, or Firm*—Burns, Doane, Swecker & Mathis

[57] ABSTRACT

A new and distinct variety of Green Ash tree named Cimmzam is provided. The new variety can be readily distinguished from the typical *Fraxinus pennsylvanica* Green Ash treen (nonpatented in the United States). For instance, the new variety generally is a stronger grower which forms a trunk and branches having a larger diameter; forms lateral branches which leave the tree at a lesser angle and in a more uniform pattern; form leaves that are larger, thicker, and darker in coloration; forms new foliage in the spring later and drops its leaves in the fall later; and exhibits a distinctive fall foliage coloration pattern. Such fall foliage coloration successively changes from deep burgundy to apricot to orange-yellow. The new variety is particularly well suited for growing as attractive ornamentation and well serves as a distinctive and colorful shade tree for growing in the landscape.

6 Drawing Sheets

SUMMARY OF THE INVENTION

The new and distinct variety of Fraxinus Green Ash tree was discovered during 1968 as a seedling of unknown parentage while growing in a cultivated area tended by man. More specifically, the new variety was discovered while growing among trees of the Green Ash (*Fraxinus pennsylvanica*) being grown on the Sustar Farm, located at Perry, Oh. in Zone 6a. The seed parent of the new variety is believed to be *Fraxinus pannsylvanica* and the pollen parent is unknown.

My attention was initially attracted to a single plant of the new variety since it was found to exhibit a combination of characteristics which differ significantly from those of the typical Green Ash tree. Had I not discovered and preserved this new tree it would have been lost to mankind.

It has been found that the new and distinct Green Ash tree of the present invention exhibits the following combination of characteristics:

(a) exhibits stronger growth characteristics and forms a trunk and lateral branches of a larger diameter than the typical *Fraxinus pennsylvanica,*

(b) forms lateral branches which leave the tree at a lesser angle and in a more uniform pattern than the typical *Fraxinus pennsylvanica,*

(c) forms leaves that are larger, thicker, and darker in coloration than the typical *Fraxinus pennsylvanica,*

(d) forms leaves in the spring later than the typical *Fraxinus pennsylvanica,*

(e) drops its leaves in the fall later than the typical *Fraxinus pennsylvanica,* and (f) exhibits a distinctive fall foliage coloration which successively changes from deep burgundy to apricot to orange-yellow.

Trees of the new variety have been asexually reproduced by budding onto *Fraxinus pennsylvanica* understocks. The characteristics of the new variety have been found to be strictly transmissible by such asexual propagation from one generation to another.

The new variety has been named the Cimmzam variety. Also, trees of the new variety are being marketed of Perry, Ohio, under the Cimmaron trademark.

BRIEF DESCRIPTION OF THE PHOTOGRAPHS

The accompanying photographs show as nearly true as it is reasonably possible to make the same in color illustrations of this character, typical specimens of the tree and plant parts of the new variety. All specimens depicted were grown at Perry, Ohio.

Figure 9:
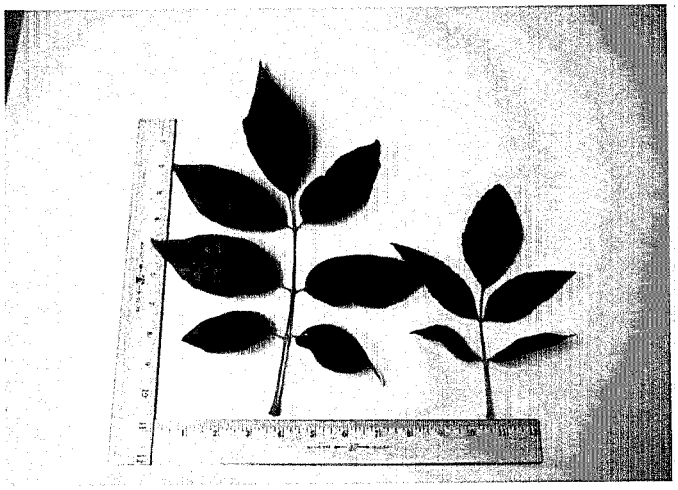

FIG. 9 illustrates for comparative purposes a representative leaf of the new variety on the left and a representative leaf of the Summit Green Ash variety on the right. The photograph was made during early October and the darkening of the leaf coloration is attributable to the fall environment. The disparity in leaf sizes is apparent.

Figure 10:
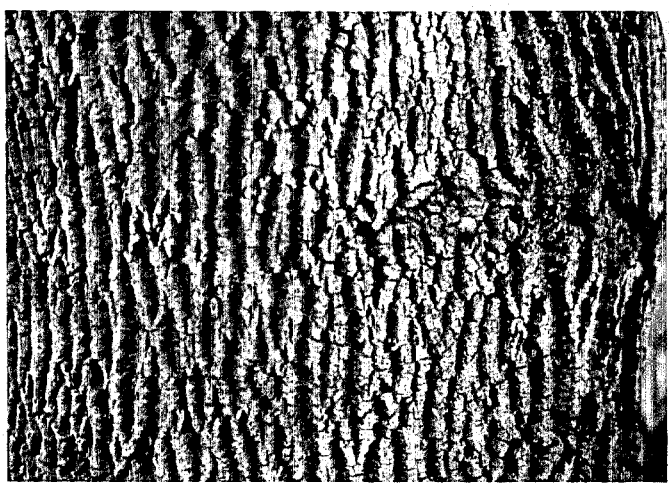

FIG. 10 illustrates the typical appearance of the bark of the original tree of the new variety.

DETAILED DESCRIPTION

The chart used in the identification of colors is that of The Royal Horticultural Society (R.H.S. Colour Chart). Other references to color are to be accorded their ordinary dictionary significance. The descriptions are based upon trees grown at Perry, Ohio.

Figure 1:
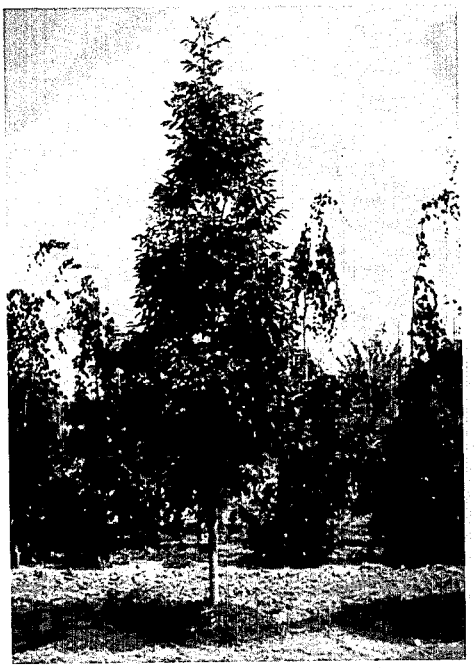
FIG. 1 illustrates a three-year old tree of the new variety.
Figure 2:
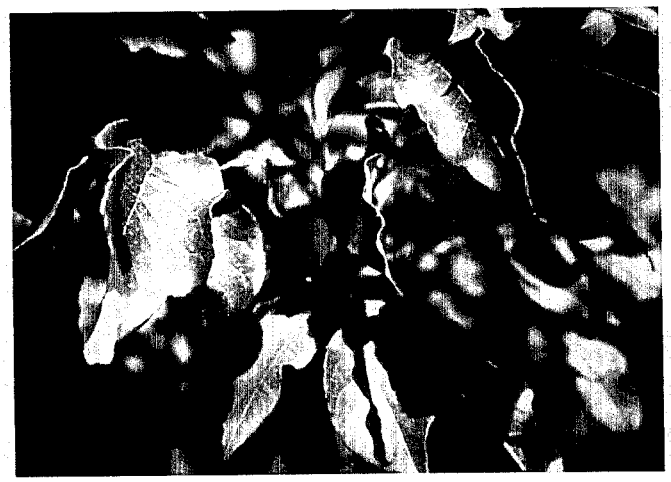
FIG. 2 illustrates a close-up view of the summer foliage.
Figure 3:
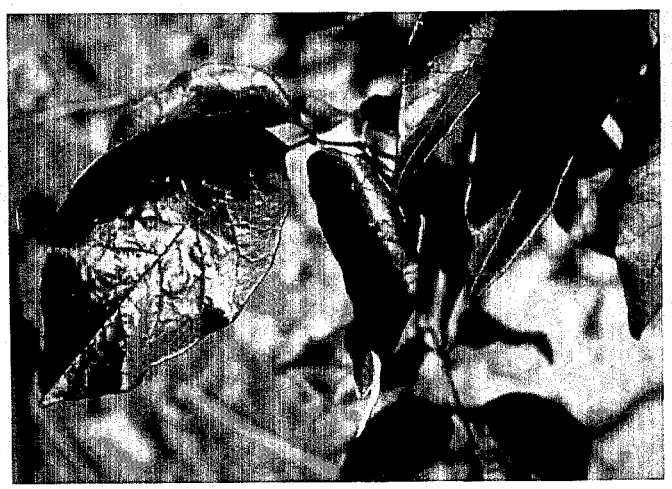
FIG. 3 illustrates a close-up view of the foliage showing the beginning of the first stage of fall coloration wherein traces of deep burgundy coloration have begun to appear.
Figure 4:
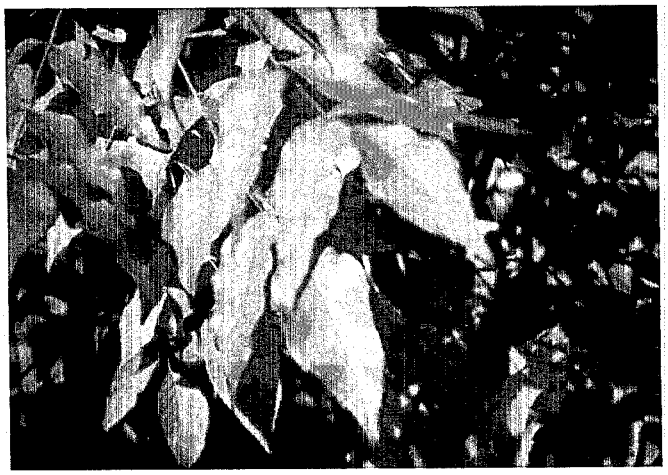
FIG. 4 illustrates a close-up view of the foliage showing the second stage of fall coloration wherein apricot coloration is present.
Figure 5:
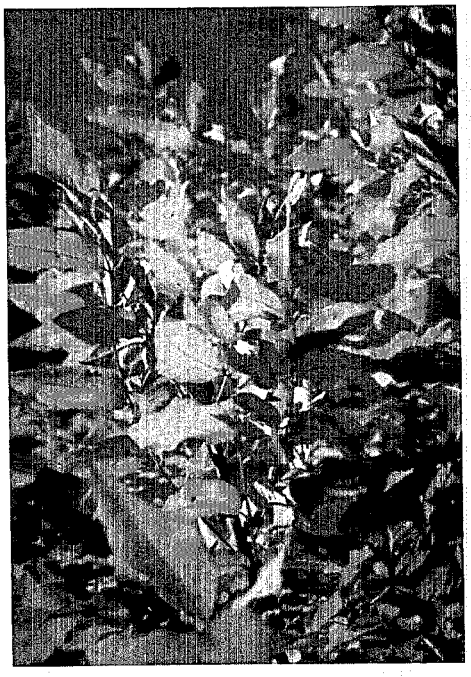
FIG. 5 illustrates a close-up view of the foliage showing the third or mature stage of fall coloration wherein a bright orange-yellow coloration is present.
Figure 6:
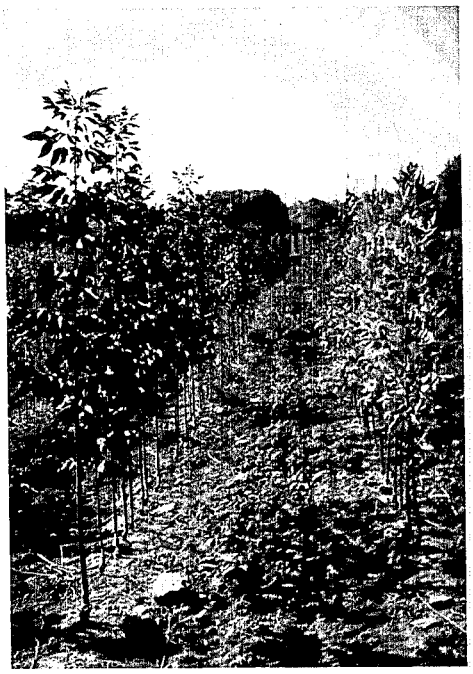
FIG. 6 illustrates a row of one year old trees of the new variety on the left during the stage of the fall coloration as compared to the Summit variety of *Fraxinus pennsylvanica lanceolata* Green Ash tree on the right.
Figure 7:
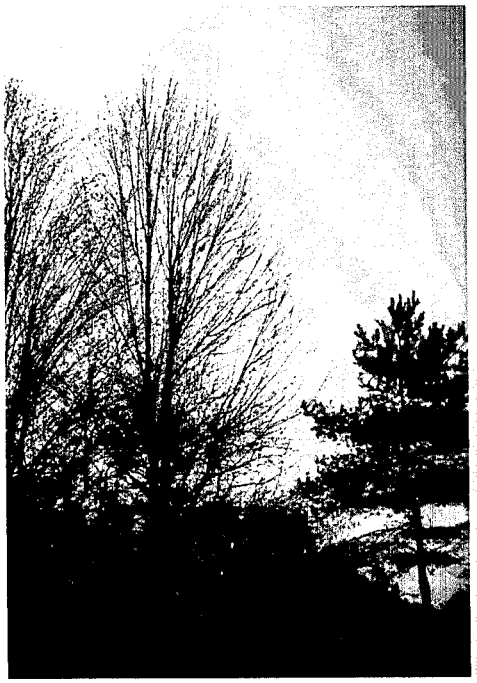
FIG. 7 illustrates at the left center during the winter the original tree of the new variety wherein its growth habit is apparent.
Figure 8:
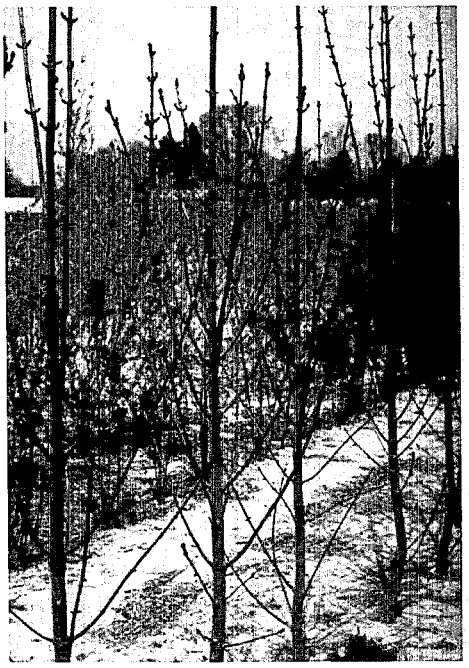
FIG. 8 illustrates during the winter a row of two year old trees of the new variety wherein the branching structure is apparent.

The original tree of the new variety is presently approximately 40 feet tall, is approximately 20 feet wide, and has a caliper of approximately 18 inches at grade. Accordingly, the new variety exhibits a broadly pyramidal growth habit as illustrated in FIG. 7. When grown on its own roots, the tree is expected to reach a height of approximately 60 feet and a width of approximately 30 feet at full maturity. A central leader is formed. The density of branching or canopy is similar to that of the Summit variety (nonpatented in the United States).

The new variety exhibits stronger growth characteristics and more vigor at an early age when compared to other closely related varieties. As it matures, its vigor tends to approximate that of other known Green Ash varieties. For instance, a one year-old whip of the new variety when grown at Perry, Ohio, commonly will be approximately 4 to 6 inches greater in height than the Summit variety (nonpatented in the United States), and commonly exhibits a caliper which is approximately ¼ inch greater.

The new variety has been found to exhibit lateral branches which leave the tree at a lesser angle than those of the typical *Fraxinus pennsylvanica.* For instance, the branches of the new variety commonly ascend at an angle of approximately 20 to 30 degrees. This can be compared to an angle of approximately 30 to 40 degrees for the Summit variety (nonpatented in the United States) and of approximately 45 degrees for the Patmore variety (U.S. Plant Pat. No. 4,684) and the Wasky variety (U.S. Plant Pat. No. 7,036). Such lateral branches, along with the trunk also tend to be stronger and of a larger diameter than those of the typical *Fraxinus pennsylvanica.* The lesser branch angle exhibited by the new variety is believed to make it more resistant to storm damage since the melting snow and ice can more readily slide downwardly to the ground. This can be contrasted to branches having a more horizontal disposition which tend to retain snow and ice to a greater degree.

The vegetative and reproductive parts of the variety are decidedly different than those of the typical Green Ash tree. The leaves commonly are somewhat involute, opposite, pinnately compound, ovate to lanceolate, have undulation at the peripheral portions of the blades, and tend to be substantially larger and thicker than those of the typical Green Ash tree. The leaf coloration during mid-season commonly approximates that of Yellow-Green Group 147A on the upper surface and tends to be somewhat paler on the under surface. The leaves generally have a broadly cuneate base and commonly end in an acuminate tip. The leaf margins are entire or indistinctly crenate.The leaf midrib coloration is generally consistent with that of the species; however, the rachis has a bright red coloration during the fall which is not common to the Green Ash. When initially formed the light green leaf blades are pubescent and mature to a glabrous, dark green coloration while remaining pubescent underneath. The compound leaves of vegetative shoots commonly reach a length of up to approximately 14 inches and commonly contain 3 to 9 leaflets which are approximately 3 to 6 inches in length and approximately 1½ to 2½ inches in width. The leaflet stalks of the new variety are generally approximately 1/16 inch longer than those of the species, and of the Summit variety (nonpatented in the United States) in particular. The immature twigs are light brown in coloration with small whitish/orange lenticels which persist with age. Two-year old twigs tend to be a medium chocolate brown in coloration. Winter buds are a red to medium chocolate brown in coloration and generally are wooly.

Continuing observations of the new variety have confirmed that flowers are formed which are apetalous, campanulate, and deep red wine-purple and green in coloration. However, no seeds have been observed to date.

In the spring, the leaves of the new variety generally emerge approximately 3 to 5 days later than the typical *Fraxinus pennsylvanica.*

In the fall, the leaves of the new variety generally drop approximately 7 to 10 days later than the typical *Fraxinus pennsylvanica.* The first stages of fall coloration of my new variety commonly appear on approximately September 1st at Perry, Ohio, while the typical *Fraxinus pennsylvanica* commonly does not begin to assume fall coloration until approximately October 1st. The coloration of the first stage the fall leaf coloration of my new variety is deep burgundy and approximates that of Greyed-Purple Group 187A. The second stage of the fall leaf coloration is apricot and approximates that of Greyed-Orange Group 170A and 170B. The third or mature stage of fall leaf coloration is orange-yellow and approximates that of Greyed-Orange Group 167A through 167D. In comparison the typical *Fraxinus pennsylvanica* foliage turns a bright yellow in the fall.

The leaf scars of the new variety measure approximately ¼ inch in width, are opposite, semicircular, and are rounded across the top with a shallow notch, and the vascular bundle traces are arranged in a "C" shape. This can be contrasted to the Wasky variety (U.S. Plant Pat. No. 7,036) and the species in general where the vascular bundle traces tend to be somewhat flattened across the top. Such a rounded leaf scar is typical of the White Ash (i.e., *Fraxinus americana*). Accordingly, it may be possible that the pollen parent was the White Ash. However, the identity of the pollen parent continues to be unknown.

The winter buds of the new variety are broadly ovoid, scurfy, approximately ⅛ inch in length, brownish in coloration, and are somewhat slightly downy. They commonly include 1 to 3 pairs of opposite, overlapping bud scales. A terminal bud commonly is present and stipule scars are lacking.

The mature bark of the new variety is thick and grayish-black in coloration as illustrated. It has deep longitudinal furrows, and irregularly shaped areas separated by flat scaly ridges.

The Cimmaron variety can be readily distinguished from other closely related varieties of *Fraxinus pennsyl-*

*vanica,* including the Wasky variety (U.S. Plant Pat. No. 7,036), the Patmore variety (U.S. Plant Pat. No. 4,684), and the Summit variety (nonpatented in the United States). For instance, its branch angles are distinctive and the fall leaf coloration can readily be used to distinguish these varieties. The leaves of the common Green Ash, the Patmore variety, and the Summit variety change to yellow in the fall, and the leaves of the Wasky variety change to bronze-red in the fall. As previously indicated, the leaves of the new variety change from deep burgundy to apricot to orange-yellow in the fall. Also, the leaves of the new variety tend to be retained on the tree longer in the fall than those of the Summit variety.

When grown at Perry, Ohio, the new variety has exhibited disease resistance and has not been affected to any degree by diseases and insects which are common to Fraxinus. The new variety has proven to be hardy to Zone 3 of the USDA Hardiness Map which can experience an average minimum winter temperature of −30° to −40° F. It is being grown satisfactorily in Zones 3b, 4a, and 6a. While being grown at Perry, Ohio, it was exposed to a low temperature of −18° F. on Jan. 21, 1985, without any known deleterious impact. Also, considerable drought resistance has been exhibited by the new variety. For instance, the average annual precipitation at Perry, Ohio, is understood to be 35.4 inches. In two out of the last four years the area has experienced severe drought conditions. In 1988 the annual precipitation was only 29.67 inches and in 1991 the average precipitation was only 32.67 inches. The new variety withstood these conditions with no known damage.

I claim:

1. A new and distinct variety of Green Ash tree which exhibits the following combination of characteristics:

(a) exhibits stronger growth characteristics and forms a trunk and lateral branches of larger diameter than the typical *Fraxinus pennsylvanica,*
(b) forms lateral branches which leave the tree at a lesser angle and in a more uniform pattern than the typical *Fraxinus pennsylvanica,*
(c) forms leaves that are larger, thicker, and darker in coloration than the typical *Fraxinus pennsylvanica,*
(d) forms leaves in the spring later than *Fraxinus pennsylvanica,*
(e) drops its leaves in the fall later than the typical *Fraxinus pennsylvanica,* and
(f) exhibits a distinctive fall foliage coloration which successively changes from deep burgundy to apricot to orange-yellow;

substantially as herein shown and described.

* * * * *